United States Patent [19]

Christensen et al.

[11] Patent Number: 4,657,755

[45] Date of Patent: Apr. 14, 1987

[54] COMPOSITION AND METHOD FOR INVESTIGATING ALIMENTARY FUNCTIONS

[75] Inventors: Finn N. Christensen, Copenhagen; Jens R. Jensen, Stenløse; Helle Bechgaard, Hellerup, all of Denmark

[73] Assignee: A/S Alfred Benzon, Copenhagen, Denmark

[21] Appl. No.: 568,184

[22] PCT Filed: Apr. 22, 1983

[86] PCT No.: PCT/DK83/00047
§ 371 Date: Dec. 21, 1983
§ 102(e) Date: Dec. 21, 1983

[87] PCT Pub. No.: WO83/03762
PCT Pub. Date: Nov. 10, 1983

[30] Foreign Application Priority Data

Apr. 23, 1982 [DK] Denmark .............................. 1839/82

[51] Int. Cl.$^4$ .................... A61K 43/00; A61K 49/00; A61K 49/02
[52] U.S. Cl. .......................................... 424/1.1; 424/4; 424/5; 424/9; 424/79
[58] Field of Search ...................... 424/1.1, 4, 5, 9, 79

[56] References Cited

U.S. PATENT DOCUMENTS

| | | | |
|---|---|---|---|
| 2,611,730 | 9/1952 | Heming | 424/79 |
| 3,368,944 | 2/1968 | Sandmark et al. | 424/4 |
| 3,780,171 | 12/1973 | Irmscher et al. | 424/79 |
| 4,107,283 | 8/1978 | Pratt et al. | 424/1.1 |
| 4,115,540 | 9/1978 | Digenis et al. | 424/1.1 |
| 4,193,985 | 3/1980 | Bechgaard et al. | 424/4 |
| 4,243,652 | 1/1981 | Francis | 424/1.1 |
| 4,350,675 | 9/1982 | Drake | 424/1.1 |

OTHER PUBLICATIONS

Jakovljevic et al, Chemical Abstracts, vol. 99 (1983) #35342j.
Theodorakis et al, J. Null. Med., 23 (1982) 693-7.

Primary Examiner—Christine M. Nucker
Attorney, Agent, or Firm—Stiefel, Gross, Kurland & Pavane

[57] ABSTRACT

Enterically administrable diagnostic compositions for investigating alimentary functions comprising multiple units of a size of at the most 5 mm, preferably between 0.5 and 1.3 mm in particular between 0.7 and 1.0 mm, each unit comprising a tracer substance binding agent (such as an ion exchange resin) with a radioactive tracer substance with a half-life of at the most 5 days, in particular $^{99m}$Tc, $^{113m}$In, $^{111}$In and $^{129}$Cs, is associated. The tracer substance binding agent is being formulated with pharmaceutically acceptable excipients, in particular granulating excipients, in such a way that the exposure of the gastrointestinal mucosa to the tracer substance binding agent is reduced and that the units do not disintegrate during the passage through the gastrointestinal tract. Preferred units comprise cross-sectionally substantially homogeneous multi-component cores in which the tracer substance binding agent is granulated with one or more excipients and which are optionally coated.

Preferred units comprise cross-sectionally substantially homogeneous multi-component cores made by granulating the tracer-binding agent surface properties. Tracer substances are normally present in an amount from about 2 to about 20% by weight, preferably from about 5 to about 10% by weight, calculated on the units. Due to low leaching and the non-disintegrating properties, the composition can be used to investigate gastric emptying also of the last 20% of a food bolus, cf. FIG. 2 which illustrates the average gastric emptying pattern for 7 healthy volunteers (A) compared to the emptying from a person with the "Giesskannen" phenomenon (B).

22 Claims, 2 Drawing Figures

COMPOSITION AND METHOD FOR INVESTIGATING ALIMENTARY FUNCTIONS

FIELD OF INVENTION

The present invention relates to a composition and method for investigating alimentary functions.

BACKGROUND OF INVENTION

The methods most widely used today for investigating alimentary functions and visualization of the alimentary canal comprise the use of radioopaque contrast media. However, the use of radioopaque media with X-rays to determine gastric emptying time or intestinal transit time, or to monitor the passage of material through the alimentary canal will subject the patient to high energy radiation in amounts which are often undesirable and furthermore offer only limited information on the functioning of the alimentary canal.

The radioopaque agent which is most often used for investigation of the gastrointestinal tract is barium sulphate, normally administered as a viscous suspension. Barium sulphate, however, has several disadvantages for this purpose. In particular, barium sulphate is known to change the movement of materials through the various parts of the intestines, which means that the results obtainec by using barium sulphate can hardly be taken as an indication of the functional state of the intestinal system, resulting in inadequate or even faulty diagnosis, which further results in inappropriate treatment.

It is also known to use soluble iodine compounds having a high radiodensity, typically tri-iodinated substituted benzene compounds, as X-ray contrast media for investigation of the alimentary canal. However, also with these agents, the patient will be subjected to undesirable amounts of high energy radiation.

Methods which do not rely upon the use of X-rays for the determination of gastrointestinal transit time have been used inert compounds such as carbon black and chromic oxide. In these methods, however, the transit time is determined by determining the interval between the time of an oral dose and the time of appearance of the compound in faces, and this means that no visualization of the alimentary canal and no differential diagnosis of the functional state of the various regions of the gastro-intestinal tract are obtained.

It is known from U.S. Pat. No. 4,115,540 and U.S. Pat. No. 4,243,652 that certain $\gamma$-emitting radionuclides can be used in combination with certain carriers to provide multiple-units radiodiagnostic agents for investigation of the alimentary canal be scintigraphy which is normally performed noninvasively by means of a suitable instrument such as a $\gamma$-camera or a rectilinear scanner, etc. It is also known to prepare single-unit tablets labelled with e.g. $^{131}I$ or $^{99m}Tc$ for investigating the behaviour of pharmaceutical functions in the gastrointestinal tract.

BRIEF DISCLOSURE OF INVENTION

The present invention utilizes pharmaceutical formulation techniques to provide compositions and methods for investigating alimentary functions, which compositions and methods are advantageous over the prior art compositions.

In one aspect, the invention relates to an enterically administrable diagnostic composition for investigating alimentary functions comprising multiple units of a size of at the most 5 mm, each unit comprising a tracer-substance for binding binding agent to which a diagnostically acceptable radioactive tracer substance with a half-life of at the most 5 days suitable for detection of the position of the unit in the alimentary system, and the radioactive tracer substance associated therewith. The tracer substance for binding the radioactive tracer is formulated with at least one pharmaceutically acceptable excipient in such a way that, when the composition is administered, the exposure of the gastrointestinal mucosa to the substance binding agent is reduced, and in such a way that the units do not disintegrate during their passage through the gastrointestinal tract. Other aspects of the invention relates to a method for making a labelled diagnostic composition, a composition designed to be labelled with tracer substance, and a method of investigating alimentary functions as will be explained in the following.

The composition of the invention is a multiple-units composition, i.e. a composition which is administered as a multiplicity of units, generally at least 50 units, which will be distributed in the gastrointestinal tract in a reproducible statistical manner, in contrast to the stochastic behaviour associated with single-unit compositions.

The tracer substances of the labelled units of the present invention are tracer substances with a half-life of at the most 5 days. In contrast to with a longer half-life tracer substances used in some of the known compositions, the tracer substances of the present invention minimize the risk of long-term radiation injury for both the patient and the staff involved in the investigations.

The formulaton with the pharmaceutically acceptable excipient provides a number of advantages. Firstly, by formulating the tracer binding substance with a pharmaceutically acceptable excipient, any problems associated with the properties of the particular substance binding are minimized. Thus, for instance, binding substance which are not proven non-toxic and therefore not approved by the health authorities for direct exposure to the gastrointestinal mucosa may nevertheless be used in the composition of the invention. This is especially an advantage as most binding substances, as will appear from the list blow, are substantially insoluble compounds for which, generally speaking, only local toxic effects caused by the tracer binding substances contact with the mucosa will have to be considered. Due to the formulation of the composition of the invention, such contact is substantially avoided. A further advantage of formulating the binding substance with a pharmaceutically acceptable excipient in such a way that the exposure of the gastrointestinal mucosa to the binding substance is reduced is that this protects the gastrointestinal mucosa from local irritation by the binding substance. Another advantage is that the amount of the binding substance in the composition may be varied and thus optimally adapted to the particular tracer substance. One of the most important features of the composition of the invention is that by means of the pharmaceutical excipient or excipients, a number of parameters which are determinative of the transition behaviour of the units in the gastrointestinal tract, i.e. size, size distribution, density, and surface properties, may be varied at will to provide compositions which are optimal for their particular diagnostic purposes, independent of the binding substance employed. Thus, in contrast to barium sulphate, the composition of the invention can be formulated in such a way that it will neither coat nor adhere to the mucous membranes throughout the alimentary canal.

As will appear from the following, a further advantageous feature of the composition of the invention is that it may easily be formulated in such a manner that the labelling of the composition by combining the binding substance with a radioactive tracer substance may be performed in a simple manner, even by unskilled staff, at the site of use whereby handling and transport of the labelled and hence radioactive composition is avoided. One advantage associated with this is that the amount of radioactivity administered with the units can be varied at the hospital or the laboratory, thus permitting optimization of the radioactivity for the particular investigation in question.

A still further important feature of the composition of the invention is that the formulation with one or several pharmaceutical excipients reduces radioactive leaching from the units which would otherwise impair the scintigraphic detection. Thus, for instance, when the composition of the invention is used for determination of gastric emptying, a sufficiently low degree of leaching may be secured to significantly reduce or entirely obviate the systematic error which in the known art use of tracer substance alone arises from leaching of free tracer substance. Thereby, it becomes possible, for example, to determine a true solid phase gastric emptying and not a mixed gastric fluid/solid phase emptying.

Examples of conditions for which it has been found or is contemplated that they may be diagnosed by means of the composition of the invention are colonic functional diseases, sigmoid diseases, constipation, Crohn's disease, diarrhea, duodenal diseases such as duodenal ulcer, ileal diseases, intestinal obstruction, malabsorption syndromes such as blind loop syndrome and tropical sprue, esophageal ulcer, esophageal functional diseases such as esophageal reflux and esophageal stenosis, dumping syndrome, the "Giesskannen" phenomenon (an apparently harmless abnormality in the duodenum characterized by reduced mobility of the descending part of the duodenum), stomach diseases such as pyloric stenosis and gastric ulcers, and functional effects of gastrointestinal operations such as anastomosis, and various vagotomies, resections, ileostomies or colostomies.

The present invention permits the monitoring of the passage of the food-simulating units through the alimentary canal and makes it possible not only to investigate the transit time through the entire alimentary canal, but also to investigate the transit time in segments of the alimentary canal individually. Thus, utilizing the composition of the present invention, the following transit times can be investigated and diagnosed, either individually or in combination:

Esophageal transit time, gastric emptying time, small intestine transit time, including the individual transit times in duodenum, jejunum, and ileum, and colonic transit time, including the individual transit times in the ascending, transverse and descending colon as well as in the sigmoid flexure or the rectum.

Further, the present invention makes it possible to investigate the mixing of the contents in the various parts of the gastrointestinal tract. An example is that it is possible to investigate the movement of stomach contents from the fundus to the antrum or investigate the effectivity of the mixing in the various parts of the small intestines or in the various parts of the large intestines.

This differentiation of the investigation and diagnosis of the alimentary canal transit times and mixing effectivity permit a very detailed and individualized diagnosis of the alimentary conditions mentioned above.

A special advantage of the present invention is that it allows co-administration of at least two formulations differing in their physical aspects such as size, surface characteristics and/or density, the different formulations being labelled with different tracer substances. This co-administration of the different formulations enables one to investigate the behaviour of each formulation separately without having to take the intrasubject variation into account as this variation will normally be so pronounced that no conclusions concerning the differences in the behaviour of the two formulations can be drawn. The co-administration is especially advantageous in view of the fact that the day-to-day variation of the transit time throughout the various parts of the gastrointestinal tract is known to be considerable and varies with conditions normally difficult to control such as the food ingested during the days prior to the investigation, the physical and mental activity level of the subjects and the emotional state of the subjects.

DETAILED DESCRIPTION OF INVENTION

Units

The composition of the invention when administered will normally be one which has a known behaviour with respect to passage through the alimentary canal of a reference animal, in particular a human being. The behaviour of a particular composition with respect to passage through the alimentary canal of a reference animal, in particular a human being, may be determined by means of scintigraphy as described herein.

The units employed in the diagnostic composition of the invention may be of various types. One example is units comprising the binder for the tracer substance coated with a pharmaceutically acceptable coating which is substantially insoluble in gastrointestinal fluids, but which is of a type which permits diffusion of the tracer substance for binding with a binding substance. Alternatively, the units may comprise cores of one or more excipients and a binding substance combined in such a way that, when the composition is administered, the exposure of the gastrointestinal mucosa to the binding substance is reduced. In this latter embodiment, the binding substance may either be applied to the surface of the cores, optionally together with an adhesive to ensure that the binding substance is retained on the cores, in which case the cores are coated with a pharmaceutically acceptable coating as stated above. According to a preferred embodiment, the cores may be cross-sectionally substantially homogeneous multi-component cores containing a binding substance granulated with one or more granulating excipients in such a way that, when the composition is administered, the exposure of the gastrointestinal mucosa to the binding substance is reduced, optionally coated with a pharmaceutically acceptable coating.

Although the granulating excipient or excipients incorporated in the core together with a binding substance may in themselves be sufficient to ensure that only a small number of the normally powdery particles of binding substance will actually be in touch with the mucosa, it is normally advantageous, depending on the type of or the amount of binding substance incorporated (particularly when the ratio of tracer-binding agent to the other ingredients is high), to coat the cores with a coating as stated above in order to further reduce the exposure of the gastrointestinal mucosa to a binding substance causing local irritation.

Units comprising multi-component cores with incorporated binding substance may additionally comprise a binding substance and optionally an adhesive applied to the surface of the cores. In this case, the cores are necessarily coated as stated above.

It will be evident from what is stated above that one of the special advantages of the multi-component cores lies in their variability. Thus, it is possible to vary any one of the different parameters involved, such as the type and amount of binding substance, and the size, surface characteristics or density of the units, without concomitantly having to alter any other parameter. For instance, the units of the present invention have the advantage over the known radiodiagnostic compositions that they may comprise several binding substances in the same unit, each of which is adapted to associate with a different tracer substance. Such units may therefore be adapted to any desired diagnostic purpose requiring isotopes of varying half-lives, or different investigations which, with the known compositions, would have to be performed successively, thus requiring repeated dosages of radioactive substances. Each dosage comprising a different isotope, as well as a prolonged investigation period, may be performed simultaneously by incorporating different isotopes in the same unit of the invention. This means that the production of the units may be standardized even though they may serve a variety of diagnostic purposes.

Alternatively or simultaneously, it may be desired to vary the size of the units.

The units may have a size in the range of between 0.05 and 5 mm, but for most of the usual purposes, the units will have a size between 0.3 and 5 mm, preferably a size between 0.3 and 2 mm, and a size range which will often be preferred is one in which the individual units are between 0.5 and 1.3 mm, in particular between 0.7 and 1.0 mm. The units will often be administered in two size ranges according to their purposes, the units of each size range being labelled with different isotopes.

By means of the units of the present invention it has now been made possible to investigate the movement of particles of solid food through the gastrointestinal tract. This is in contrast to the known particles, the size of which was too small to permit any such investigation or which were subject leaching.

The size of any one of the types of units stated above may thus be varied, although it is easier to obtain size variations with the multicomponent cores due to the method of their production.

In accordance with a particular aspect of the invention, the density of the cores, and thus, the time of appearance of the cores in the predetermined segment of the intestine may be varied at will. (Bechgaard, H & Ladefoged, K (1978): "Distribution of Pellets in the Gastrointestinal Tract. The Influence of Transit Time Exerted by the Density or Diameter of Pellets". *J. Pharm. Sci.* 69, 1327-1330).

The units of the composition can be varied with respect to their density by including various pharmaceutically acceptable excipients capable of giving the density in question. For most purposes, the units will have a density in the range of 0.5-2.5 g/ml, in particular 0.9-1.7 g/ml. Examples of excipients which may be used to increase the density of the cores are described in U.S. Pat. No. 4,193,985 and include heavy particulate substances such as barium sulphate, titanium oxide, zinc oxides, and iron salts.

Through variations of the density of the units of the composition of the invention, it is possible to make the multiplicity of the units behave distinctively differently in the gastrointestinal system. Thus, when the units have a density of approximately 1.0 g/ml, the units will float on top of the gastric fluids and thus be impeded from emptying for several hours, whereas units with a density of 1.6 g/ml will sink down into the antrum part of the stomach immediately upon administration, after which the units will empty very slowly. When co-administered, the two types of units will behave in a clearly different way as can be seen from the examples.

A special advantage of the composition of the invention is that the surface characteristics of the units can be varied according to the pharmaceutical coating chosen. Further, the surface characteristics can be varied by inclusion of surfactants or by inclusion of specifically binding substrates in the coating composition.

Binding Agents and Tracer Substances

In contradistinction to the known radiodiagnostic compositions, it is not required that the associated between the binding substance and the tracer substance be insoluble, as, even if the association dissolves within the unit, the composition can be formulated so that the components will not be released to the surrounding gastrointestinal environment due to the other components contained in the unit, either in the form of a coating or in the form of granulating excipients substantially compacting the association within the units. In this way, the leaching of the radioactive tracer substance from the units is significantly reduced. (However, it is generally preferred that the binding substance be selected so that its association with the tracer substance in the units is a solid substance having a low degree of diffusability from the composition.) Nor, as mentioned above, is it required that the binding substance be proven a non-toxic substance as, through the formulation with excipients, it can be ensured that only a minor amount of binding substance, preferably none, comes into contact with the gastrointestinal mucosa. Thus, a wider range of binding substances may be employed.

Binding substance which may be used for the purpose of the present invention are normally selected from the group consisting of ion exchangers, including ion exchange and synthetic resins, and hydroxyapatite, diphosphonates, anionic starch derivatives, sulphur colloids, phytate colloids, pyrophosphates, organic phosphonates, organotin complexes, macroaggregated serum albumins, metal hydroxide colloids, pyridoxals, phospholipids, diethylenetriaminepentaacetic acid, polyamine polymers formed from polystyrene, and triethylene tetramine, and rose bengal. The binding substance is preferably an anionic ion exchange resin, the functional groups of which are secondary or tertiary aliphatic amines or quarternary ammonium groups with a $pK_a$ value of the resin of more than 8, or a cationic ion exchange resin, the functional groups of which are sulphonic acid or carboxylic acid groups with a $pK_a$ value of the resin of less than 8. If the binding substance employed is a cationic ion exchange resin, it may be charged with, for instance, sodium ions or be in the acidic form.

The binding substances may be present in the units of the composition of the invention in amounts ranging from as little as about 0.1% to as much as about 95% by weight calculated on the units, depending on the character of the binding substance the construction of the units with respect to the position of the binding substance, etc. Normally, the binding substance will be present in amounts from about 2 to about 60% by weight, preferably 2–20% by weight, such as 2–10% by weight, in particular 5–10% by weight calculated on the units.

The tracer substance is preferably a substance having a high quantum yield of a relevant scintigraphically determinable radiation, such as a quantum yield of at least 25%, preferably a quantum yield of above 50%, more preferably a quantum yield of above 80% of the total radiation.

If the quantum yield is substantially lower than stated above, the necessary dose to the patient in order to obtain a sufficient scintigraphic detection within a sufficiently short time would be so high that it would not be acceptable from a dosimetric point of view (which, for brevity, in the present specification and claims is included in the concept "diagnostically acceptable").

Also, in order to meet the requirement of administering the minimum necessary radioactive dose in order to prevent radiation injury, the present invention provides compositions incorporating tracer substances specifically chosen for their relatively short half-lives which are still compatible with the diagnostic purposes in question.

The dose (D) from an isotope depends in the following way on the total administered activity (A) and the effective half-life of the isotope in the body ($T_{\frac{1}{2}\ eff.}$) (Rocha AFG and Harbert JC (1978): "Textbook of Nuclear Medicine: Basic Science", Lea & Febiger, Philadelphia). $D \propto T_{\frac{1}{2}\ eff.} \times A$ $$T_{\frac{1}{2}\ eff.} = \frac{T_{\frac{1}{2}\ iso} \times T_{\frac{1}{2}\ bio}}{T_{\frac{1}{2}\ iso} \times T_{\frac{1}{2}\ bio}}$$

As seen from the expression, keeping in mind that the biological half-life of the isotope ($T_{\frac{1}{2}\ bio}$) depends only on the total transit time (time from mouth to anus), A and $T_{\frac{1}{2}\ iso}$ should be kept as low as possible at the same time. However, in order to get good pictures (sufficiently high counting rates), a certain amount of activity is necessary. In order to investigate gastric conditions, an isotope with a half-life of a few hours, e.g. $^{113m}$In ($T_{\frac{1}{2}\ iso}=1.7$ h), will usually be sufficient. When the functioning of the intestines is to be investigated, e.g. small intestinal transit time, it may be necessary to use an isotope with a somewhat longer half-life such as $^{99m}$Tc ($T_{\frac{1}{2}\ iso}=6.03$ h), and to determine the total transit time $^{129}$Cs ($T_{\frac{1}{2}\ iso}=32$ h) or $^{111}$In ($T_{\frac{1}{2}\ iso}=67$ h) is optimal. However, in no instance will it be necessary to use an isotope of a half-life of more than 5 days. The composition of the invention is thus distinguished from some of the known radiodiagnostic compositions which use isotopes, the half-lives of which are not shorter than 27 days (vide U.S. Pat. No. 4,107,283), as these known art compositions are made by methods where the tracer substance is included in the composition by the manufacturer whereas in the composition of the invention, the tracer substance is applied at the site of use substantially immediately prior to use.

Examples of diagnostically acceptable tracer substances which fulfil the above criteria are well-known in clinical practice. Specific examples of diagnostically acceptable tracer substances are substances, the active principle of which is selected from the group consisting of $^{99m}$Tc, $^{113m}$In, $^{111}$In, and $^{129}$Cs. An example of a tracer substance which, due to a too low quantum yield, is not diagnostically acceptable is $^{51}$Cr, which has a quantum yield of about 8%.

It is an important advantage of the invention that the units of the invention can be formulated so that they are capable of binding the tracer substance to such an extent that the radioactive leaching from the units is below the values which would tend to impair the scintigraphic detection. Thus, for example, when the composition of the invention is used for determination of gastric emptying, the leaching is so low that it significantly reduces or completely obviates the systematic error which in the known art use of associated tracer alone arises from the leaching of free tracer substance. Gastric emptying half-time is normally on the order of from a few minutes to some hours, depending upon whether the food is fluid or solid, and the leaching of radioactivity from the units during this time should be sufficiently low so that it does not significantly reduce the gastric emptying time measured. This is especially critical with isotopes like $^{99m}$Tc administered in the form of pertechnetate because the pertechnetate absorbed from the lumen of the gastrointestinal tract would be secerned in the stomach or accumulated in the bladder or in the thyroid gland.

One particular advantage of the composition of the invention is that it may be formulated so that the leaching is sufficiently low even over prolonged periods to permit reliable investigations of the intestinal system where transit half-times are on the order of several hours, and even reliable investigations of the colonic system where transit half times are of the order of more than 10 hours. Thus, as will appear from the results stated in the working examples, low leaching ratios have been measured on compositions of the invention even after very prolonged immersion in artificial intestinal fluid. As will further appear from the results in the working examples, leaching from the composition of the invention was not even detectable in vivo. Hence, the compositions of the invention constitute a new and reliable tool for scintigraphic determination of the functions of the alimentary canal.

A special advantage of the invention is that it permits a simple labelling procedure at the site of use such as the laboratory or hospital, which procedure normally merely comprises immersing the units in a solution containing an effective concentration of the tracer substance for a period of time sufficient to bind an effective amount of tracer substance to the tracer-binding agent, for example for a few hours or simply overnight, removing the solution from the labelled units, e.g. by means of a needle and syringe and simply rinsing excess tracer substance solution from the units with water or saline solution. This means that when using the composition of the invention, the radioactive tracer-generating systems which are generally already available in hospitals or laboratories may be utilised for preparing the solution of tracer substance, thus avoiding transport and minimizing handling of the labelled and hence radioactive composition.

Furthermore, the simple labelling procedure reduces the radioactive doses to which the staff performing the labelling is exposed, to an absolute minimum.

The radioactivity of the labelled units will normally be in the range of 5–500 μCi, in particular about 50 μCi per dosage of the units to be administered.

Cores

In one embodiment, each unit comprises a core or a carrier material with binding substance applied to its surface. The carrier material may be a pharmaceutically acceptable natural or synthetic wax, e.g. paraffin wax, or a sugar in which case the core is a so-called "non-pareil" core. In a particular embodiment, the units are made from paraffin wax by breaking the paraffin wax into small particles, heating said particles to soften the surface and applying the binding substance by powdering.

These cores may, however, suffer from a number of disadvantages, mainly with respect to size and density variations which, in the "non-pareil" cores, are limited by the available standard cores.

Therefore, the most preferred embodiment is one in which a cross-sectionally substantially homogeneous multi-component core contains the binding substance granulated with one or more granulating excipients. In this type of core, microparticles of the binding substance are mixed with one or more excipients in such a way that, over a cross-section of the core body, the same type of composition is present.

The use of cross-sectionally substantially homogeneous cores offers several advantages.

Firstly, cross-sectionally substantially homogeneous cores are easy to produce on a large scale in reproducible manner in, e.g., automatic equipment because the components therefor are normally simply mixed in the prescribed proportions, which means that the inter-core variation in composition, e.g., concentration of binding substance can be kept within narrow limits. Secondly, the concentration of binding substance in the core can be varied within very wide limits (preferably between 2 and 60% by weight) and thus variation in the amount of tracer substance may be similarly varied. Thirdly, the size and density of the cores may be easily adjusted as desired.

The granulating excipients used to prepare the multi-component cores comprise one or more substances selected among carbohydrates and derivatives thereof such as sugars, e.g. lactose or sucrose, starch and starch derivatives, and microcrystalline cellulose, lubricants and fillers such as silicates, e.g. Bolus Alba or talc, or calcium stearate, binders such as cellulose derivatives including methylcellulose and hydroxypropylmethylcellulose, and polyethylene glycol, polyvinylpyrrolidone, agar or gelatin, and density-increasing substances such as barium sulphate, titanium oxide, zinc oxides and iron salts.

The cores are typically made by granulating particles of the binding substance together with excipients, including bulk agents such as carbohydrates and derivatives thereof such as starch and starch derivatives, including microcrystalline cellulose, binders such as cellulose derivatives, including methylcellulose or hydroxypropylmethylcellulose, polyethylene glycol, polyvinylpyrrolidone, agar, or gelatin, such as by treatment in a high speed mixer (to directly obtain compact-shaped cores), or by treatment in a planetary mixer with subsequent extrusion of the mixture into strings of predetermined diameter close to the desired final cross-sectional dimension of the cores and treatment of the strings in a marumerizer or similar equipment to obtain compact-shaped cores.

When the cores are cross-sectionally substantially homogeneous cores, the binding substance is normally incorporated in the cores during the manufacturing of the cores as described above. Alternatively, or combined therewith, the tracer binding agent may be applied on the surface of the cores, optionally using an adhesive such as hydroxypropylmethylcellulose.

Coating

When the binding substance agent is so situated that it is completely or partially exposed, it is necessary to provide the cores or particles of binding substance with a coating which will protect the gastrointestinal mucosa from local irritation caused by the binding substance. This is particularly necessary when the binding substance is an ion exchange resin, some of which would be a local irritant if ingested without the protective coating. Even when the binding substance is contained within a multi-component core so that only a minor amount of it is exposed, it is, for most purposes, preferred that the units of the composition of the invention be coated. The coating is a pharmaceutically acceptable coating which is substantially insoluble in gastrointestinal fluids, and which is of a type which permits diffusion of the tracer substance for binding with a binding substance.

The basic ingredient of the coating is a film-forming excipient which is normally selected from cellulose derivatives, acrylic polymers and copolymers, vinyl polymers, and other high molecular polymer derivatives or synthetic polymers such as ethylcellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, coumarone-indene polymer, polybutadiene, vinyl chloride-vinyl acetate copolymer, ethylene-vinyl acetate copolymer and vinyl chloride-propylene-vinyl acetate copolymer or a combination thereof. Preferred film-forming excipients are ethyl cellulose or a polymerisate of acrylic acid ethyl ester and methacrylic acid methyl ester, e.g. the so-called Eudragit ® coatings.

The coating may optionally comprise other pharmaceutically acceptable materials which improve the properties of the film-forming excipient such as plasticizers, anti-adhesives, diffusion-accelerating substances or diffusion-retarding substances.

Often, it is preferred to plasticize the coating with a plasticizer such as a plasticizer selected from e.g. glyceryl triacetate, acetyltriethyl citrate, acetyl-tributyl citrate, propyleneglycol, polyethyleneglycol and castor oil. A coating which has been found to function well in practice is a coating comprising ethyl cellulose plasticized with acetyltributyl citrate.

The amount of coating applied on the units is normally in the range between about 1% and 50% by weight, calculated on the weight of the coated units, often preferably in the range from about 2% to about 20%, calculated on the same basis.

Generally, a thicker coating will necessitate a longer soaking period in the labelling solution, but will, on the other hand, reduce any leaching into the alimentary tract.

The techniques used in these methods, including the binders, lubricants, fillers, etc., correspond to the techniques and excipients used in the normal pharmaceutical preparaton of corresponding multiple units formulations.

In another aspect, the invention relates to a diagnostic composition adapted to be labelled with a radioactive tracer substance, comprising multiple units of a size of at the most 5 mm, each unit comprising an ion exchange resin which is formulated with at least one pharmaceutically acceptable granulating excipient in such a way that, when the composition is administered, the exposure of the gastrointestinal mucosa to the ion exchange resin is reduced, that the units do not disintegrate during their passage through the gastrointestinal tract, and further that at least part of the binding substance is accessible, by permeation, to a solution containing a tracer substance. The ion exchange resin is present in an amount of 2–60%, in particular 2–20%, by weight, calculated on the unit. The units are coated with a pharmaceutically acceptable coating which is substantially insoluble in gastrointestinal fluids, but which permits difusion of the tracer substance for binding with the binding substance.

In particularly favourable embodiments of the composition of the invention, each unit contains a binding substance which is capable of binding at least two different tracer substances in the composition of the invention or at least two tracer binding substances, each of which is capable of binding a different tracer substance, or the composition comprises two different types of unit each of which contains a different binding substance capable of binding a different tracer substance. Optionally, the units may have different physical characteristics with respect to density, surface and/or size. These features, obtainable only by means of the present invention, have the advantage of providing compositions which may be used for simultaneous investigations of the alimentary system, thus eliminating the intraperson variation occurring when two different types of units differing in said physical characteristics are compared, as described in detail above. The tracer substances are preferably selected from $^{99m}$Tc, $^{113m}$In and $^{111}$In.

Similarly, the composition according to the invention can be in such a manner that the units are capable of binding at least three tracer substances, either due to each unit containing a multiplicity of binding substances, or due to the composition being a mixture of units each of which is capable of binding one or several tracer substances, the units optionally having different physical characteristics with respect to density, surface and/or size. This aspect of the invention offers the same advantages as mentioned above, but in this case it will be possible to compare three different types of units, e.g. units with three different densities without having to take the intrasubject variation into account. The three tracer substances are selected from $^{99m}$Tc, $^{113m}$In, $^{111}$In and $^{129}$Cs. The reason why these tracer substances are selected is that their quantum yield is high (100%), their half-lives are relatively short and they offer energy spectra which can be distinguished on the scintigraphic device in question, e.g. a γ-camera with two or more channels, by proper window setting of the channels eventually followed by mathematical calculations correcting for overlapping between the window setting for a tracer substance and the energy spectra of the other tracer substances.

Another aspect of the present invention is a method of investigating alimentary functions, comprising administering multiple units of a size of at the most 5 mm to an animal, in particular a human being, and determining the distribution or position of the units at intervals by a determination method utilizing the radioactive emission from the units. Each unit comprises a binding substances to which a diagnostically acceptable radioactive tracer substance with a half-life of at the most 5 days suitable for detection of the position of the unit in the alimentary system is associated, the binding substance being formulated with at least one pharmaceutically acceptable excipient in such a way that, when the composition is administered, the exposure of the gastrointestinal mucosa to the binding substance is reduced, and in such a way that the units do not disintegrate during their passage through the gastrointestinal tract. The determination is usually performed by a scintigraphic method, such as by means of a γ-camera or a scintillation counter. By means of this method, it is possible to perform individual investigations of one or several regions of the alimentary canal. Also, this method has the advantages of convenience to hospital or laboratory staff due to the simple labelling, and of safety, i.e. causing the staff and patients to be only minimally exposed to radiation as well as causing no local irritation of the patient's gastrointestinal tract as discussed above.

A further aspect of the invention relates to a method of investigating alimentary functions, comprising administering at least two types of units which are labelled with different diagnostically acceptable radioactive tracer substances and which have different physical characteristics with respect to density, surface and/or size simultaneously or sequentially, and selectively determining the distribution or position of units of each type. This method makes it possible to investigate the influence of various factors, e.g. the physical characteristics of the pellets, on the transit time through or mixing of the luminal content in various parts of the gastrointestinal tract. Such investigations have hitherto been either extremely costly and time-consuming or simply impossible due to the intraperson variation. Through the elimination of intraperson variation obtained by this method of the present invention, such investigations have been made possible as will appear from the following examples.

MATERIALS AND METHODS

Figure 1:
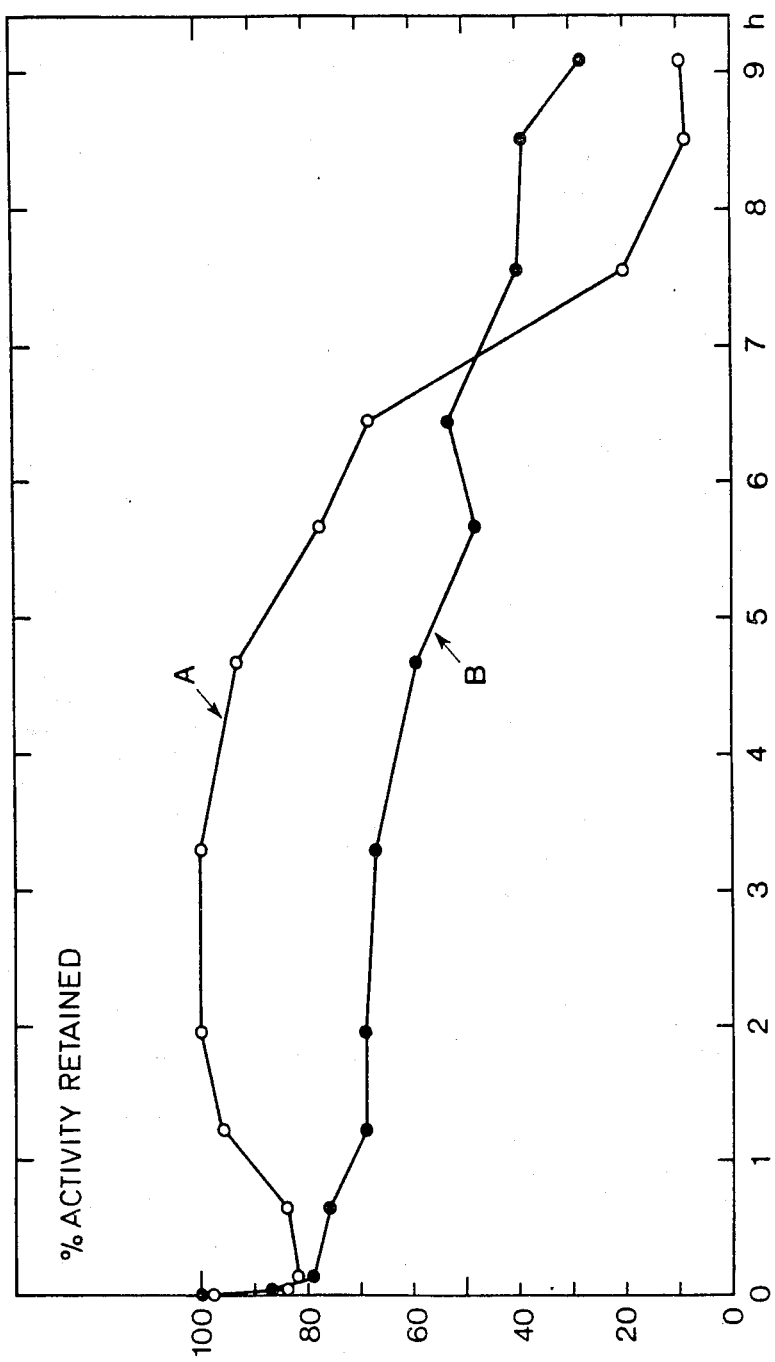
FIG. 1 illustrates the gastric emptying pattern of two formulations differing in density (open circles: density 1.0 g/ml, closed circles: density 1.6 g/ml), labelled with two different isotopes and co-administered to a volunteer.

In the examples, the following materials were used:

| | |
|---|---|
| Barium sulphate | Ph Eur |
| Bolus Alba | Ph Eur |
| Microcrystalline cellulose | BPC 79 |
| Calcium stearate | USP XX |
| Talc | Ph Eur |
| Purified water | Ph Eur |
| Ethyl cellulose | NFXV |
| Paraffin | NFXV |
| Amberlite ® CG400 | Anion exchanger from Rohm & Haas, 75–150 μm, chloride form |

| | -continued |
|---|---|
| Amberlite ® CG 120 | Cation exchanger from Rohm & Haas, 75-150 μm, sodium form |
| Acetyltributylcitrate | Citroflex ® A-4; supplied by Pfizer A/S, Copenhagen, Denmark |
| Isopropanol | BP 80 |
| Polyvinyl-pyrrolidone | BP 80 Add 81 |
| $99m$Tc generator | Tecegen ® from Hoechst (100 mCi) |
| $111$In solution | Carrier-free indium trichloride, activity 4 mCi/ml, from Amersham |
| Mixobar ® | X-ray contrast agent: barium sulphate suspension, 0.6 g/ml, from Astra-Meditec |
| Density measurements: | Were performed as Hg densitometry |
| Scintillating | Was performed in a NaI(Tl) crystal counter (well type), BP 80 |
| Dose calibration: | Was performed in a Mediac ® Dose calibrator from Nuclear-Chicago. |
| Artificial stomach and intestinal fluids: | Were prepared according to USP XX (excluding enzymes) |
| γ-Camera I: | International General Electric MAXI II having a 40 cm field and fitted with a 400 keV parallel hole collimator. |
| γ-Camera II: | International General Electric MAXI 161 having a 39 cm field and fitted with a low energy parallel hole collimator interfaced with a General Electric Star analysis system. |
| Activity calculations: | The counts were corrected for background, radioactive decay and dead time. (parker, R P, Smith, P H S & Taylor, D M "Basic Science of Nuclear Medicine" (1978); Churchill Livingstone; Edinburgh) |

EXAMPLE 1

Labelling of High Density Pellets with $99m$Tc and in vitro Testing of Leaching

Preparation of Cores of Barium Sulphate with Incorporated Binding Substance

Cores were prepared from the following ingredients:

| | |
|---|---|
| Barium sulphate | 70.0% |
| Bolus Alba | 10.0% |
| Talc | 6.0% |
| Microcrystalline cellulose | 7.0% |
| Calcium stearate | 2.0% |
| Polyvinylpyrrolidone | 2.0% |
| Ethylcellulose | 0.5% |
| Amberlite ® CG 400 | 2.5% |
| | 100.0% |

A mixture of the above ingredients was moistened with isopropanol and purified water and mixed until the mixture was a little lumpy.

The moist mixture was extruded through a 0.75 mm sieve. The resulting extrudate consisted of strings breaking off in lengths of a few cm.

The extruded strings were broken into small particles and formed into compact-shaped cores in a marumerizer.

Coating of Cores with Diffusion Coating

A diffusion coating suspension was prepared from the following ingredients:

| | |
|---|---|
| Ethylcellulose | 4.5% |
| Acetyltributylcitrate | 0.5% |
| Isopropanol | 95.0% |
| | 100.0% |

The cores were coated with 5% of the coating material (calculated as w/w of dry ingredient in the coating suspension to dry ingredient in the cores). The coating procedure was performed in a fluidized bed. Finally, the pellets were sieved (sieve fraction 0.71-1.0 mm).

Application of Gamma Emitter $99m$Tc pertechnetate solution was prepared by eluting a $99$Mo column (Tecegen ®) with a 0.9N sodium chloride solution.

0.6 g of the pellets was soaked in 0.5 ml of the eluate having a radioactivity of approximately 1.25 mCi/ml. The soaking was stopped by removing the solution by means of a needle and syringe, after which the pellets were rinsed in 1 ml of water.

In vitro Testing

Various samples of pellets were soaked for various soaking periods as appears from Table 1. Some of the samples were tested for leaching of the radioactive substance by immersion in 5 ml of artificial gastric fluid, pH 1.2, and 5 ml of artificial intestinal fluids, pH 7.5, respectively, while other samples were kept for later measurement of the radioactivity.

The radioactivity of the pellets, the soaking liquid, the rinsing liquid, and the artificial fluids was measured by counting in a gamma scintillation well counter after a period of time sufficient for the radioactivity to be within the measuring range of the counter. Based upon the measurements, the activity of each of the samples at the elution time was calculated. The results appear in Table 1.

TABLE 1

Measurement of Radioactivity in μCi, Values Calculated for Elution Time

| | | Radio activity μCi | | | | |
|---|---|---|---|---|---|---|
| Experiment No. | Soaking time | Soaking Liquid | Rinsing Liquid | Artificial gastric fluid | Artificial intestinal fluid | Pellets |
| 1 | 1 h 40 min | 208 | 60.4 | — | — | 60.9 |
| 2 | 4 h | 157 | 33.1 | — | — | 99.4 |
| 3 | 21 h | 58 | 12.4 | 2.40[1] | 10.2[2] | 237 |
| 4 | 21 h | 73 | 40.0 | 2.99[1] | 17.6[3] | 230 |
| 5 | 21 h | 46.6 | 21.4 | — | 24.6[4] | 301 |

[1]immersion 1 h
[2]immersion 17 h
[3]immersion 44 h
[4]immersion 66 h

It appears from Table 1 that it is possible to form an association between the binding substance and the radioactive tracer substance within reasonably short periods. Even a labelling period of 1 h 40 min results in a satisfactory activity of the pellets. It also appears that the release from the pellets in gastric fluid and intestinal fluid is relatively low, in view of the fact that even over a period of 66 hours in intestinal fluid, less than 10% of the radioactivity had leached.

EXAMPLE 2

Labelling of Low Density Pellets with Core-bound $99m$Tc and in vitro Testing of Leaching Preparation of Paraffin Cores with Incorporated Binding Substance Paraffin was extruded through a 0.5 mm sieve. The resulting extrudate consisted of strings breaking off in lengths of about 10 cm.

The extruded strings were mixed with 2.5% of Amberlite ® CG 400, calculated on the combined weight of the paraffin strings and the Amberlite ®. Simultaneously with the mixing, the mixture was powdered with microcrystalline cellulose to avoid adhesion between the paraffin strings. The resulting mixture was extruded five times through a 0.5 mm sieve. Between the extrusions, the strings were powdered with microcrystalline cellulose.

The strings were immersed in water and mechanically broken into small particles by means of a stirrer.

The resulting cores were coated with a diffusion coating in the same manner as described in Example 1. The amount of coating applied was 5% of coating solids, calculated on the weight of the uncoated cores.

In vitro Testing

The resulting pellets were labelled with $^{99m}$Tc and tested as described in Example 1. The activity of the fluids and the pellets was measured as described in Example 1.

The results appear in Table 2.

TABLE 2

Measurement of Radioactivity in
μCi, Values Calculated for Elution Time

| Experiment No. | Soaking time | Radioactivity μCi | | | | |
|---|---|---|---|---|---|---|
| | | Soaking Liquid | Rinsing Liquid | Artificial gastric fluid | Artificial intestinal fluid | Pellets |
| 1 | 1 h 40 min | 111 | 88.8 | — | — | 58.2 |
| 2 | 4 h | 233 | 32.4 | — | — | 42.9 |
| 3 | 21 h | X | 38.6 | 15.5[1] | 9.5[2] | 145 |
| 4 | 21 h | 110 | 7.64 | 4.2[1] | 13.0[3] | 199 |
| 5 | 21 h | 86.1 | 19.7 | 5.4[1] | 15.1[4] | 254 |

[1]immersion 1 h
[2]immersion 17 h
[3]immersion 44 h
[4]immersion 66 h
X = the particles absorbed all the soaking liquid.

It appears from the data of Table 2 (Experiments 3, 4, and 5) that the reproducibility of the labelling is not quite satisfactory, which is believed to be due to trapping of labelling fluid between the paraffin microflakes formed during the extrusions.

EXAMPLE 3

Labelling of Low Density Pellets with Surface-bound $^{99m}$Tc and in vitro Testing of Leaching Preparation of Cores of Paraffin with Substance Binding Applied on the Surface Paraffin strings were made by extruding paraffin through a 0.5 mm sieve. The resulting extrudate consists of strings breaking off at lengths of about 10 cm.

The strings were immersed in water and mechanically broken into small particles by means of a stirrer. The water was removed, and the particles were heated to approximately 35° C. Thereby, the surface of the particles softened, and 10% by weight of Amberlite ® CG 400 was added by powdering while stirring with a pestle. Thereby, about half of the Amberlite ® adhered to the surface of the particles.

The resulting cores with Amberlite ® applied at the surface were coated with a diffusion coating (5%, calculated on the weight of the cores) in the same manner as described in Example 1.

In vitro Testing

The resulting pellets were labelled with $^{99m}$Tc and tested in the same manner as described in Example 1. The activity of the fluids and the pellets was measured as described in Example 1. The results appear in Table 3.

TABLE 3

Measurement of Radioactivity in
μCi, Values Calculated for Elution Time

| Experiment No. | Interrupted after | Radioactivity μCi | | | | |
|---|---|---|---|---|---|---|
| | | Soaking Liquid | Rinsing Liquid | Artificial gastric fluid | Artificial intestinal fluid | Pellet |
| 1 | ½ h | 12.6 | — | — | — | 3.45 |
| 2 | 1½ h | 1.78 | — | — | — | 12.0 |
| 3 | 24 h | 1.03 | 0.380 | 0.337[1] | — | 10.8 |
| 4 | 24 h | 1.08 | 0.162 | — | 0.303[1] | 14.5 |
| 5 | 24 h | 1.61 | 0.141 | — | 0.15[2] | 9.45 |

[1]immersion 24 h
[2]immersion 49 h

It appears from these data that the reproducibility of the labelling is better than in Example 2. Also, it is seen that the stability of the labelling is satisfactory.

EXAMPLE 4

Labelling of Medium Density Pellets with $^{99m}$Tc and in vitro Testing of Leaching from Whole and Ground Pellets Preparation of Cores with a density of 1.3 g/ml
Cores were prepared from the following ingredients:

| | |
|---|---|
| Lactose | 30% |
| Microcrystalline cellulose | 25% |
| Sucrose | 25% |
| Hydroxypropylmethyl cellulose | 10% |
| Amberlite ® CG400 | 10% |
| | 100% |

The cores were prepared and coated with 2.5% coating suspension (percent by weight calculated as dry matter on the weight of the cores) as described in Example 1 (except that only water was used as the moistening agent). Finally, the cores were sieved, and the 1.0–1.19 mm sieve fraction was selected.

In vitro Testing of Whole and Ground Pellets $^{99m}$Tc pertechnetate solution was prepared as described in Example 1. The eluate was diluted to give 0.7 μCi/ml. Four samples (each 0.60 g) were labelled with 1 ml of the $^{99m}$Tc pertechnetate solution for 3 hours. The liquid was removed and the labelled pellets were rinsed in 4 ml isotonic NaCl solution.

Two of the samples were ground in an agate mortar, and the four samples were then placed in artificial gastric fluid (0.1N HCl solution) for 2½ h. The fluid was removed from the pellets. The activity of the pellets and the fluid were measured in the dose calibrator in order to determine leaching from the pellets. The results appear in Table 4.

TABLE 4

Leaching from Whole and Ground Pellets

| | Whole | | Ground | |
|---|---|---|---|---|
| Activity μCi pellets | 249 | 275 | 242 | 232 |
| Activity μCi fluid | 4.54 | 4.51 | 3.62 | 4.03 |
| % Leaching | 1.82 | 1.64 | 1.50 | 1.74 |
| Average leaching in % | 1.73 | | 1.62 | |

Thus, this formulation with effective granulating excipients resulted in low leaching. The coating was not observed to contribute further to the reduction of the leaching. The reason for this is probably that, due to the granulation, the resin particles are not exposed to the artificial gastrointestinal fluid to any significant extent even when ground.

EXAMPLE 5

In vitro Testing of the Effect of Coating upon Leaching from $^{99m}$Tc-Labelled Ion Exchange Resins Preparation of Uncoated and Coated Ion Exchange Resins A diffusion coating suspension was prepared from the following ingredients:

| | |
|---|---|
| Ethyl cellulose | 2.5% |
| Isopropanol | 97.5% |
| | 100.0% |

Two samples of an ion exchange resin (Amberlite ® CG 400) were coated with 24% and 50%, respectively, of coating material (calculated as w/w of dry ingredient in the coating suspension to ion exchange resin). The coating was performed in a fluidized bed.

Application of Gamma Emitter $^{99m}$Tc pertechnetate solution was prepared by eluting a $^{99}$Mo column (Tecegen ®) with a 0.9N sodium chloride solution.

2×0.3 g of an uncoated and of each of the two coated samples of ion exchange resin were soaked in 1.8 ml of the diluted eluate having a radioactivity of approximately 0.7 mCi/ml. The labelling was stopped after 3 hours by removing the solution, after which the pellets were rinsed in 4 ml isotonic NaCl solution.

In vitro Testing

The samples were tested for leaching of the radioactive substance by immersion in 5 ml of artificial gastric fluid, pH 1.0, for 2½ hours.

The fluid was removed from the resins by means of a needle and syringe. The radioactivity of the resins and the fluid was measured in the dose calibrator.

The results appear from Table 5.

TABLE 5

| Leaching from Uncoated and Coated Ion exchange Resins | | | | | |
|---|---|---|---|---|---|
| | Uncoated | | +24% coating | | +50% coating |
| Activity μCi resin | 282 | 290 | 333 | 337 | 320 | 355 |
| Activity μCi fluid | 7.0 | 5.3 | 1.8 | 3.0 | 4.0 | 4.1 |
| Average leaching, % | 2.17 | | 0.72 | | 1.21 | |

Thus, the effect of the coating is statistically significant on a 5% level as calculated by an analysis of variance.

EXAMPLE 6

In vivo Testing of the Leaching from Two Similar High Density Formulations

Preparation of Pellets

Two batches of cores were prepared as described in Example 1 with 2.5% Amberlite ® CG 120 and 2.5% Amberlite ® CG 400, respectively, thus containing two different substance binding capable of binding two different isotopes ($^{111}$In and $^{99m}$Tc). The cores were coated with the same coating solution as in Example 1, but using 20% by weight of coating solids, calculated on the weight of the uncoated cores. The two batches did not differ in their physical characteristics with respect to shape, size, density and surface.

A sample of each batch (0.80 g) were labelled with 0.22 mCi $^{111}$In and 0.80 mCi $^{99m}$Tc, respectively, for 21 hours as described in Example 1.

In Vivo Stability

The two samples were co-administered to a healthy volunteer (whose informed consent was obtained). Anterior and posterior pictures (sampling time: 1 min.) were recorded by means of γ-camera l. The subject was placed in front of the camera in a standing position.

The pictures were recorded using the "Dual isotope" facilities of the camera, thus making it possible to calculate the countings from each of the two isotopes separately. Regions of interest containing the whole of the stomach (including antrum) were drawn on the computer.

The geometric mean (of the anterior and posterior pictures) of the countings for each isotope in the regions of interest was calculated and corrected for decay and background activity.

The corrected activity in the stomach as a function of time appears from Table 6:

TABLE 6

| Corrected Activity in the Stomach as a Function of Time | | |
|---|---|---|
| Time (min.) after administration | $^{99m}$Tc % of maximum value | $^{111}$In % of maximum value |
| 3.00 | 97.91 | 98.62 |
| 19.00 | 100.00 | 98.55 |
| 44.00 | 96.70 | 100.00 |
| 60.00 | 87.27 | 96.67 |
| 85.00 | 74.74 | 74.85 |
| 100.00 | 64.46 | 78.18 |
| 110.00 | 75.53 | 77.56 |
| 120.00 | 82.71 | 82.93 |
| 130.00 | 76.57 | 75.95 |
| 147.00 | 78.55 | 80.00 |

Furthermore, pictures of thyroid and bladder were recorded, as any $^{99m}$Tc (in the form of $TcO_4^-$) leaching from the pellets would invariably be absorbed in the intestines and accumulated in these organs. No activity, neither in the thyroid nor in the bladder, was detected in the course of the study.

Thus, no activity in detectable amounts was leaching from the $^{99m}$Tc-labelled pellets and, as the $^{99m}$Tc- and $^{111}$In-labelled pellets have the same physical characteristics and thus behave similarly in the gastrointestinal tract, it may be concluded that no detectable leaching of $^{111}$In was present either, as liquid $^{111}$In would otherwise have emptied much faster from the stomach, which would have given rise to a faster emptying of the decay- and background-corrected $^{111}$In actiivity from the stomach compared to the emptying of the decay- and background-corrected $^{99m}$Tc activity.

EXAMPLE 7

Gastric Emptying of Low and High Density Pellets

Preparations

A sample (0.29 g) of pellets (density 1.0 g/ml) prepared and labelled with $^{99m}$Tc as described in Example 3 and a sample (0.80 g) of pellets (density 1.6 g/ml) prepared and labelled with $^{111}$In as described in Example 6 were tested in vivo. The two samples differed in their physical characteristics only with respect to the density as the same coating material and the same size of the individual pellets (the same sieve fraction) was used. Further, the compact shape of the individual pellets and the number of pellets in each sample were similar.

Administration

The samples were co-administered to a healthy volunteer (whose informed consent was obtained), and the activity in the stomach was registered with a γ-camera as described in Example 6.

Results

The results appear in FIG. 1. Curve A shows the activity of $^{99}$Tc in the stomach region representing the low density pellets. No activity leaves the stomach for the first 3 hours because the low density pellets tend to float on top of the stomach fluid (which could easily be seen from the γ-camera picture). But once the surface of the stomach fluid passes below the smaller stomach wall curvature, the emptying is quick. Curve B represents $^{111}$In corresponding to high density pellets. Some activity leaves the stomach relatively fast (this is not leaching as was proven in Example 6) whereas the rest of the pellets were stuck in the antrum for a long time (which could also easily be seen from the γ-camera picture).

In conclusion, the density has a significant effect upon the emptying pattern. Furthermore, the γ-camera pictures distinctly show the difference and the separation between the two types of pellets.

EXAMPLE 8

Pellets as Solid Food Markers

Preparation of Cores with a Density of 1.3 g/ml

Cores were prepared from the following ingredients:

| | |
|---|---|
| Lactose | 40% |
| Microcrystalline cellulose | 25% |
| Sucrose | 25% |
| Hydroxypropylmethyl cellulose | 5% |
| Amberlite ® CG400 | 5% |
| | 100% |

The cores where prepared and coated with 5% of coating suspension (percent by weight calculated as dry matter on the weight of the cores) as described in Example 1.

Finally, the resulting pellets were sieved and the 0.71–1.0 mm sieve fraction was selected.

Study

A sample (0.6 g) of the pellets was labelled and administered to a person (informed consent was obtained) as described in Example 5. After an overnight fast, the person was given an "Amdrup beef" (consisting of 150 g tenderloin, 150 g potatoes and 15 g butter without salt and spices) and 100 ml of Mixobar ®, which was ingested over 15 minutes. Then the pellets were administered on a spoon and the patient was further given a small amount of water. No smoking or eating was allowed during the study.

The patient was asked to lie down and turn 360°. Then the patient was asked to stand in front of the γ-camera. Anterior pictures were recorded every 15 minutes during the first 90 minutes and then every 30 minutes until no activity was left in the stomach.

Pictures were recorded with γ-camera ll. The pictures were recorded for 1 minute using the "Dynamic study" facilities of the camera. Regions of interest containing the whole of the stomach (including antrum) were drawn on the computer. The countings were corrected for decay and background activity. Furthermore, X-ray pictures were recorded.

After some hours, the γ-camera pictures showed that only about 10% of the pellets were left in the stomach whereas the X-ray pictures postulated a full stomach.

Gastroscopy

A gastroscopy was performed and two doctors independently estimated the volume of the remaining food bolus to be approximately 50 ml corresponding to approximately 10–15% of the administered volume. At the same time, the gastroscopy revealed that the inside of the stomach was coated with $BaSO_4$ in spite of the fact that Mixobar ® is acknowledged to be the least mucosa-coating $BaSO_4$ preparation available. Finally, a pellet-free sample of the bolus was aspirated through the gastroscope tube. The radioactivity of the aspirated sample was detected on the dose calibrator. No activity was detectable even though the lower detection limit of the dose calibrator is as low as 0.01 μCi, and the total dose administered was 50 μCi.

Conclusion

Thus, the radioactive pellets of the invention appear to be a far better solid food marker than is $BaSO_4$. The fact that no detectable leaching took place in vivo from the pellets of the invention shows that these may be used as reliable markers of the gastric emptying of the last 20% of a solid food bolus.

EXAMPLE 9

Diagnosing the "Giesskannen" Phenomenon (Case Story)

Study 8 samples of the pellets prepared in Example 8 were labelled as described in Example 4 and administered with 150 ml of water to 8 people who had fasted (and whose informed consent was obtained).

Pictures were recorded and data processed as described in Example 8.

Figure 2:
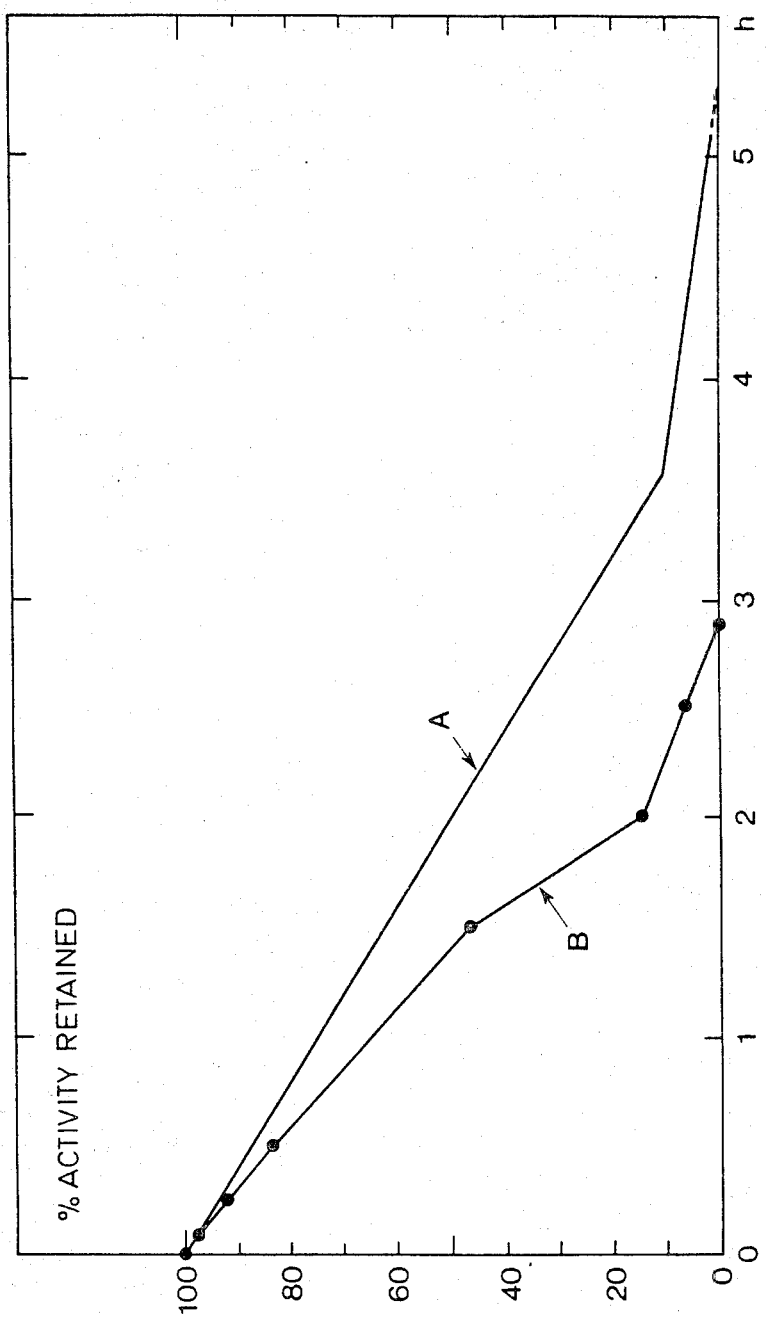
FIG. 2 illustrates the average gastric emptying pattern for 7 healthy volunteers (A) compared to the emptying from a person with the "Giesskannen" phenomenon (B). The possibility of diagnosing the "Giesskannen" phenomenon and, on the whole, the reliability of the activity values in the range below 20% retained activity are particularly valuable features of the present invention such as described herein.

The average emptying pattern observed in 7 of the 8 persons is represented by curve A in FIG. 2, whereas the last person showed the emptying pattern seen in curve B in FIG. 2.

X-ray anatomy studies of the gastrointestinal tract of said last person showed a "Giesskannen" phenomenon.

Conclusion

Thus, due to their freedom from leaching and their associated excellent capability of functioning as markers of also the last 20% of a solid food bolus, the pellets of the invention are useful as a diagnostic tool to diagnose the "Giesskannen" phenomenon.

EXAMPLE 10

Pre-Anastomosis Diagnosis (Case Story)

Medical Background

A patient who had previously undergone a parietal cell vagotomy complained of abdominal pains and vomiting after meals. When the condition was investigated by traditional diagnostic techniques (X-ray and gastroscopy) no abnormalities were revealed. The initial diagnosis was therefore a possible retention and it was considered to perform an anastomosis. However, it was decided to first diagnose his condition by means of the tracer substance-labelled pellets of the invention.

Study

A sample (0.6 g) of the pellets prepared in Example 8 was labelled as described in Example 4. The pellets were administered (with 100 ml of water instead of the Mixobar ®), the pictures recorded and the data processed as described in detail in Example 8.

Conclusion

The results showed that the patient had an unusually fast gastric emptying. As the anastomosis would have caused an even faster gastric emptying, it would probably in this case have caused the dumping syndrome to occur.

The reason the fast gastric emptying had not been detected with the X-ray techniques is presumably that the mucosa had been coated by the Mixobar ® used as contrast agent in the X-ray examination.

EXAMPLE 11

Prepyloric Ulcer (Case Story)

Study

A patient with a prepyloric ulcer was tested to see whether his gastric emptying was disturbed.

A sample (0.6 g) of the pellets prepared in Example 8 was labelled as described in Example 4. The pellets were administered with 150 ml of water. Pictures were recorded as described in detail in Example 9.

During the gastric emptying, a small hot spot was clearly visible on the screen at the same place where the ulcer was located.

Conclusion

This is a remarkable phenomenon which indicates the usefulness of the composition of the invention for determining the position of gastric ulcers. Compared to the two other major methods available for determining the position of gastric ulcers, that is, administration of a BaSO$_4$ meal and X-ray determination, and gastroscopy, both of which are counterindicated when the patient is weak, the use of the composition of the invention is highly preferred.

We claim:

1. An enterically administrable multiple-unit diagnostic composition for investigating alimentary functions, the composition comprising at least two units, each unit comprising:
    (a) a core comprising a substance for binding a diagnostically acceptable radioactive tracer substance having a half-life of five days or less and being suitable for detection of the position of the unit in the alimentary system;
    (b) the radioactive tracer substance associated with said binding substance in the core; and
    (c) a pharmaceutically acceptable coating on the core, the coating being substantially insoluble in gastrointestinal fluids and allowing diffusion of the radioactive tracer substance through the coating for association with said binding substance.

2. The composition of claim 1 in which the coating comprises a film-forming material selected from the group consisting of cellulose derivatives, acrylic polymers and copolymers, vinyl polymers, ethylcellulose, cellulose acetate, cellulose propionate, cellulose butyrate, cellulose valerate, cellulose acetate propionate, polyvinyl acetate, polyvinyl formal, polyvinyl butyral, ladder polymers of sesquiphenyl siloxane, polymethyl methacrylate, polycarbonate, polystyrene, polyester, coumarone-indene polymers, polybutadiene, vinyl chloride-vinyl acetate copolymers, ethylene-vinyl acetate copolymers, and vinyl chloride-propylene-vinyl acetate copolymers.

3. The composition of claim 1 wherein the tracer substance comprises a material selected from the group consisting of $^{99m}$Tc, $^{113m}$In, $^{111}$In, and $^{129}$Cs.

4. The composition of claim 1 comprising at least two different types of radioactive tracer substances.

5. The composition of claim 1 comprising at least two different types of binding substances.

6. The composition of claim 1 wherein a tracer substance binding agent is selected from the group consisting of ion exchangers, hydroxyapatite, diphosphonates, anionic starch derivatives, sulphur colloids, phytate colloids, pyrophosphates, organic phosphonates, organotin complexes, macroaggregated serum albumins, metal hydroxide colloids, pyridoxals, phospholipids, diethylenetriaminepentaacetic acid, polyamine polymers formed from polystyrene and triethylene tetramine, and rose bengal.

7. The composition of claim 6 wherein the tracer substance binding agent is selected from the group consisting of anionic ion exchange resins having functional groups which are secondary or tertiary aliphatic amines or quaternary ammonium groups with a pK$_a$ value of the resins of more than 8 and cationic ion exchange resins having functional groups which are sulphonic acid or carboxylic acid groups with a pK$_a$ value of the resins of less than 8.

8. The composition of claim 1, in which each coated core consists essentially of said binding substance associated with the radioactive tracer substance.

9. The composition of claim 1, in which each coated core further comprises a carrier material and wherein said binder substance is adhered to said carrier material.

10. The composition of claim 9, wherein the carrier material comprises a pharmaceutically acceptable natural or synthetic wax or a sugar.

11. The composition of claim 1, in which each coated core is a cross-sectionally substantially homogeneous multi-component core containing said binder substance granulated with a granulating excipient.

12. The composition of claim 11 wherein the granulating excipient is selected from the group consisting of carbohydrates and derivatives thereof, microcrystalline cellulose, silicates, calcium stearate, cellulose derivatives, polyethylene glycol, polyvinylpyrrolidone, agar, gelatin, barium sulphate, titanium oxide, zinc oxides, and iron salts.

13. The composition of claim 11, wherein a binder substance for the radioactive tracer substance is also located on the surface of each core.

14. The composition of claim 13, wherein the binder substance for the radioactive tracer substance in each core and the binder substance for the radioactive tracer substance located on the surface of said core are different.

15. An unlabeled multiple-unit composition useful for preparing a diagnostic multiple-unit composition labeled with a diagnostically acceptable radioactive tracer substance for investigating alimentary functions, the unlabeled composition comprising at least two units, each unit comprising:
    (a) a core comprising a substance for binding the radioactive tracer substance; and
    (b) a pharmaceutically acceptable coating on the core, the coating being substantially insoluble in gastrointestinal fluids and permitting diffusion of the radioactive tracer substance through the coating for association with said binding substance.

16. The unlabeled composition of claim 15, wherein said binding substance comprises at least one ion-exchange resin, which resin is formulated with at least one pharmaceutically acceptable granulating excipient (a)

to reduce the exposure of the gastrointestinal mucosa to the ion exchange resin following administration of the labeled diagnostic composition and (b) to prevent the unit of the labeled composition from disintegrating during its passage through the gastrointestinal tract.

17. The unlabeled composition of claim 16 comprising at least two types of ion exchange resin, each type being capable of binding a different type of tracer substance.

18. The unlabeled composition of claim 16 wherein the ion exchange resin is capable of binding more than one type of tracer substance.

19. The unlabeled composition of claim 16 comprising at least two types of units, each unit comprising a different ion exchange resin.

20. A method of preparing the diagnostic composition of claim 1, comprising:
    (a) immersing a multiple-unit composition comprising at least two units, each unit comprising a core comprising a substance for binding a pharmaceutically acceptable radioactive tracer substance, the core being coated with a pharmaceutically acceptable coating which allows diffusion of the radioactive tracer substance through the coating, in a solution of the radioactive tracer substance for a sufficient period of time to bind an effective amount of the radioactive tracer substance to said binding substance; and
    (b) separating the labeled composition from the solution of the radioactive tracer substance.

21. The method according to claim 20, wherein the composition is immersed in the solution of the radioactive tracer substance substantially immediately prior to use.

22. The method according to claim 20, wherein the composition is immersed in the solution of the radioactive tracer substance for a sufficient period of time to obtain radioactivity of between 5 and 500 uCl per dosage of the units to be administered.

* * * * *

UNITED STATES PATENT AND TRADEMARK OFFICE
CERTIFICATE OF CORRECTION

PATENT NO. : 4,657,755

DATED : April 14, 1987

INVENTOR(S) : Finn N. Christensen

It is certified that error appears in the above-identified patent and that said Letters Patent is hereby corrected as shown below:

Col. 1, line 4, Abstract: after "1.3mm" insert a comma --,--.
Col. 1, line 5, Abstract: "tracer substance binding agent" should read --tracer binding substance--.
Col. 1, line 6, Abstract: after "with" insert --which--.
Col. 1, line 9, Abstract: "tracer substance binding agent" should read --binding substance--.
Col. 1, lines 12-13: Abstract: "tracer substance binding agent" should read --binding substance--.
Col. 1, line 17, Abstract: "tracer substance binding agent" should read --binding substance--.
Col. 1, line 27: "obtainec" should read --obtained--.
Col. 1, line 39: "been" should be deleted.
Col. 1, line 43: "faces" should read --feces--.
Col. 1, line 68: to Col. 2, line 1: "tracer-substance for binding agent to which" should read --substance for binding--.

Col. 2, line 6: before "substance" delete --tracer--.
Col. 2, line 10: "substance binding agent" should read --binding substance--.
Col. 2, line 32: "formulaton" should read --formulation--.
Col. 2, line 38: "substance" should read --substances--.
Col. 2, line 43: "blow" should read --below--.
Col. 2, line 46: "substances" should read --substance--.

Col. 5, line 41: "purposes" should read --purpose--.
Col. 5, line 48: before "leaching" insert --to--.
Col. 6, line 24: "associated" should read --association--.
Col. 6, line 45: "substance" should read --substances--.
Col. 7, line 2: after "substance" insert a comma --,--.
Col. 10, line 2: "tracer binding agent" should read --binding substance--.
Col. 10, line 6: after "substance" delete "agent".
Col. 10, line 64: "preparaton" should read --preparation--.

UNITED STATES PATENT AND TRADEMARK OFFICE
CERTIFICATE OF CORRECTION

PATENT NO. : 4,657,755

DATED : April 14, 1987

INVENTOR(S) : Finn N. Christensen

It is certified that error appears in the above-identified patent and that said Letters Patent is hereby corrected as shown below:

Col. 11, line 15: "difusion" should read --diffusion--.
Col. 11, line 67: "substances" should read --substance--.
Col. 13, line 14: after "Scintillating" insert --counting--.
Col. 13, line 26: capitalize "parker".
Col. 15, lines 46-47: "Substance Binding" should read --Binding Substance--.
Col. 17, line 62: "substance binding" should read --binding substances--.
Col. 18, line 51: "activiity" should read --activity--.
Col. 22, lines 5-6, Claim 6: "tracer substance binding agent" should read --said binding substance--.
Col. 22, lines 15-16, Claim 7: "tracer substance binding agent" should read -- said binding substance--.
Col. 23, line 11, Claim 18: "the" should read --one--.

Signed and Sealed this

Third Day of May, 1988

Attest:

DONALD J. QUIGG

Attesting Officer

Commissioner of Patents and Trademarks